(12) United States Patent
Kao et al.

(10) Patent No.: US 7,717,274 B2
(45) Date of Patent: May 18, 2010

(54) DEVICE AND METHOD FOR PREPARING WASHED RED BLOOD CELLS FOR NEWBORN TRANSFUSIONS

(75) Inventors: Yuan-Shiang Kao, Metairie, LA (US); Cynthia Eicher, New Orleans, LA (US)

(73) Assignee: The Board of Supervisors of Louisiana State University and Agricultural and Mechanical College, New Orleans, LA (US)

( * ) Notice: Subject to any disclaimer, the term of this patent is extended or adjusted under 35 U.S.C. 154(b) by 668 days.

(21) Appl. No.: 10/864,586

(22) Filed: Jun. 9, 2004

(65) Prior Publication Data

US 2005/0274679 A1 Dec. 15, 2005

(51) Int. Cl.
*B04B 15/06* (2006.01)
*A61K 35/14* (2006.01)

(52) U.S. Cl. .............. 210/512.1; 210/515; 422/72; 422/101; 422/102; 422/103; 494/27

(58) Field of Classification Search ............ 494/27; 422/72, 101, 102, 103; 210/787, 512.1, 514, 210/515, 516, 517, 518

See application file for complete search history.

(56) References Cited

U.S. PATENT DOCUMENTS

| | | | |
|---|---|---|---|
| 3,813,223 A * | 5/1974 | Fleck .................. 422/102 |
| 4,040,959 A | 8/1977 | Berman et al. |
| 4,567,748 A | 2/1986 | Klass et al. |
| 4,917,804 A | 4/1990 | Franks et al. |
| 5,407,425 A | 4/1995 | Werner et al. |
| 5,663,051 A | 9/1997 | Vlasselaer |
| 5,725,763 A | 3/1998 | Bonhomme et al. |
| 6,544,162 B1 | 4/2003 | Van Wie et al. |
| 6,835,353 B2 * | 12/2004 | Smith et al. .................. 422/102 |
| 2002/0185186 A1 * | 12/2002 | Juliar et al. ............... 138/96 R |

* cited by examiner

*Primary Examiner*—David A Reifsnyder
(74) *Attorney, Agent, or Firm*—Joseph P. Mueller; Adams and Reese LLP

(57) ABSTRACT

A newborn transfusion cell washing device generally comprising a disposable, graduated test tube shaped container having a cap with an inlet port, an injection/sampling port, a suction port, and a vent. The container is capable of being inserted into a conventional clinical centrifuge. The device requires a relatively small volume to operate, 25 ml or less per procedure, and can be performed easily by any hospital blood bank technologist without any special skills. Washed RBCs can be provided to the patient in a timely manner, without the need for "fresh blood." Any in-dated RBCs can be washed to remove excessive potassium and other toxins. The main RBC aliquot can be saved and repeatedly sampled until the unit is expired or exhausted. This provides a cost savings to the hospital and more importantly, minimizes the recipient's donor exposure.

17 Claims, 1 Drawing Sheet

DEVICE AND METHOD FOR PREPARING WASHED RED BLOOD CELLS FOR NEWBORN TRANSFUSIONS

STATEMENT REGARDING FEDERALLY SPONSORED RESEARCH OR DEVELOPMENT

Not Applicable

FIELD OF THE INVENTION

Newborns, and in particular, premature newborns, present unique problems with respect to transfusions. Newborn infants are more susceptible to some of the complications associated with blood and blood product administration. The present invention relates to a device that addresses the problems associated with neonatal blood transfusions. More specifically, it relates to a device and method for washing red blood cells prior to newborn transfusions due to medical concerns that include increased potassium concentrations that develop with storage.

BACKGROUND OF THE INVENTION

The early stages of infancy, and in particular, the neonatal period, are periods of rapid cell growth and proliferation. Consequently, oxygen consumption is high compared to that of older children and adults. During these early stages, there is a limitation on the infant's ability to increase stroke volume; thus, cardiac output and oxygen delivery are dependent on heart rate.

In the newborn infant, cerebral blood flow is pressure-passive; as a result, cerebral blood flow tracks perfusion pressures more closely than older patients. In addition, the circulatory system of the developing brain has watershed areas that are particularly vulnerable to ischemia and/or hypoxia. Inadequate oxygen delivery can result in the development of hypoxic/ischemic encephalopathy, the major cause of long-term neurological disorders in children.

With regard to oxygen carrying capacity, the oxyhemoglobin dissociation curve of fetal hemoglobin is shifted to the left; this provides a physiologic advantage to the fetus but may be disadvantageous in post-natal life since oxygen release at the tissue level may be impaired. Neonatal transfusions are often performed in critically ill newborns to increase tissue oxygen delivery by decreasing the P50 (oxygen tension at half saturation of blood) and improving release at the tissue level.

To further complicate the neonatal period, the increase in arterial oxygen partial pressure (PaO2) that occurs following the initiation of air breathing is sufficient to shut down erythropoietin synthesis and release. In the normal term infant, significant red cell production will only resume after "physiologic anemia" develops between 6-12 weeks after birth.

For premature infants, anemia may have more immediate and deleterious significance. In the first few weeks of embryogenesis, fetal erythrocytes are produced in the yolk sac. This site is succeeded by the fetal liver, which, by the end of the first trimester, has become the primary site of erythropoiesis. Bone marrow then begins to take on a more active role in producing erythrocytes. By approximately 32 weeks' gestation, the burden of erythrocyte production in the fetus is shared evenly by the liver and bone marrow. By 40 weeks' gestation, the marrow is the sole erythroid organ. Premature delivery does not accelerate the ontogeny of these processes.

Shortened red blood cell life span or hemolysis also contributes to premature neonatal anemia. The average life span of a neonatal RBC is only one half to two thirds that of the RBC life span in an adult. Cells of the most immature infants may survive only 35-50 days. The shortened RBC life span of the neonate is a result of multiple factors, including diminished levels of intracellular ATP, carnitine, and enzyme activity; increased susceptibility to lipid peroxidation; and increased susceptibility of the cell membrane to fragmentation.

Finally, blood loss may contribute to the development of premature neonatal anemia. If the neonate is held above the placenta for a time after delivery, a fetal-placental transfusion may occur. More commonly, because of the need to closely monitor the tiny infant, frequent samples of blood are removed for various tests. Because the smallest patients may be born with as little as 40 mL of blood in their circulation, withdrawing a significant percentage of an infant's blood volume in a short period is relatively easy. Taken together, the premature infant is at risk for the development of anemia because of limited erythrocyte synthesis, diminished RBC life span, and increased loss of RBCs. With regard to treatment, packed red blood cell (PRBC) transfusions continue to be the mainstay of therapy for premature neonatal anemia.

In addition to anemia, hyperkalemia may also complicate the first few days in very low birth weight infants. Hyperkalemia (serum potassium level>6 mEq/L) usually presents within the first 72 hours of life and is the result of immature distal tubular function and a state of relative hypoaldosteronism with a compromised ability to excrete potassium. It may also be due, in part, to a shift of potassium from the intracellular space to extracellular space associated with a decrease in Na+–K+–ATPase activity. In sick newborn infants with renal dysfunction, hyperkalemia may occur, particularly when combined with metabolic acidosis and a hypercatabolic state. Rarer causes of hyperkalemia include hypoadrenal crises, massive hemolysis, tissue damage or excessive administration of potassium as drugs or intravenous fluids. Doctors often request washed red blood cells for patients with hyperkalemia.

SUMMARY OF THE INVENTION

Packed Red Blood Cell (PRBC) transfusions account for the largest use of blood products in Neonatal Intensive Care Units (NICU). Infants, particularly those less than 1500 grams at birth are among the most common of all transfusion recipients. Most of these infants are exposed to multiple donors, and although each transfusion carries a low risk of an adverse outcome, the cumulative risk is not trivial. Transfusion practices vary among the differing NICUs; however, red blood cell transfusions are generally performed to maintain a level of hematocrit believed to be most desirable for each neonate's clinical status.

As stated above, infants with anemia of prematurity often require transfusions with PRBCs. This is usually based on the presence of symptoms compatible with anemia such as increased episodes of apnea and/or bradycardia, feeding difficulty, diminished growth, lethargy or hypotonia. Given the decreased RBC cell survival, suppression of erythropoiesis, and dilution of existing cells due to growth, these infants are often transfused to attempt to avoid problems.

Red blood cell products are typically stored using one of three anticoagulants. Blood using citrate-phosphate-dextrose (CPD) as the anticoagulant has an outdate of 21 days. Blood using citrate-phosphate-dextrose-adenine (CPDA-1) as an anticoagulant has an outdate of 35 days. If ADSOL, an anticoagulant preservative, is added to CPD blood, the shelf-life is extended to 42 days. The PRBC unit (approximately 250 cc) is divided into only 3 aliquots. Traditionally, only "fresh" blood has been used in the NICU because of concerns about the increased potassium concentrations that develop with storage, the marked decrease in 2,3-diphosphoglycerate (2,3 DPG) that occurs with storage, the drop in pH, and the viability of cells transfused through small venous catheters. However, washing packed red blood cells prior to transfusions has been used to remove some of the potassium and other toxins that might accumulate with storage as well as the presence of additives used to store the blood.

The concentration of potassium increases with increasing length of storage in bags of packed red blood cells. In addition to that lost with storage and aging, irradiation increases the amount of potassium lost by the red blood cell. In addition to potassium, 2,3-diphosphoglycerate (2,3 DPG) is also lost from the red blood cells. 2,3 DPG is a highly charged anion that alters the affinity that hemoglobin has for oxygen. It is in part responsible for the lower affinity that adult RBCs have for oxygen compared to fetal RBCs.

Presently, there is a limitation of present technology with regard to washing red blood cells. Conventional cell washing equipment can be quite expensive and are typically only found at blood centers or large hospitals. Smaller and more remote hospitals rely on regional blood centers for their supply of washed RBC's, which often are not supplied in a timely manner. In addition to the expense, the size of the machine presents further problems. Conventional cell washing equipment typically require 75-100 ml of blood product to operate. Once RBCs are washed, they have a 24-hour expiration. Since the volume of RBCs required for a neonatal transfusion is on the order of 10-20 ml, waste of the blood product is a concern. Further compounding the problem is the expense of a unit of RBCs. Thus, there is a need for a simple device that can be used to wash small volumes of red blood cells at any hospital.

Accordingly, a cell washing device is provided that generally comprises a sterile, disposable, graduated test tube shaped container having a cap with an inlet port, an injection/sampling port, a suction port, and a vent. The test tube shaped container is preferably a conical bottom plastic centrifuge tube. The vent may also comprise a hydrophobic air filter. The container is capable of being inserted into a conventional clinical centrifuge. The device requires a relatively small volume to operate, 25 ml or less per procedure, and can be performed easily by any hospital blood bank technologist without any special skills. Thus, washed RBCs can be provided to the patient in a timely manner. Furthermore, there is no need for "fresh blood" each time a neonate requires a transfusion. Any in-dated RBCs can be washed to remove excessive potassium and other toxins. The main RBC aliquot can be saved and repeatedly sampled until the unit is expired or exhausted. This provides a cost savings to the hospital and more importantly, minimizes the recipient's donor exposure.

PREFERRED EMBODIMENTS OF THE INVENTION

Figure 1:
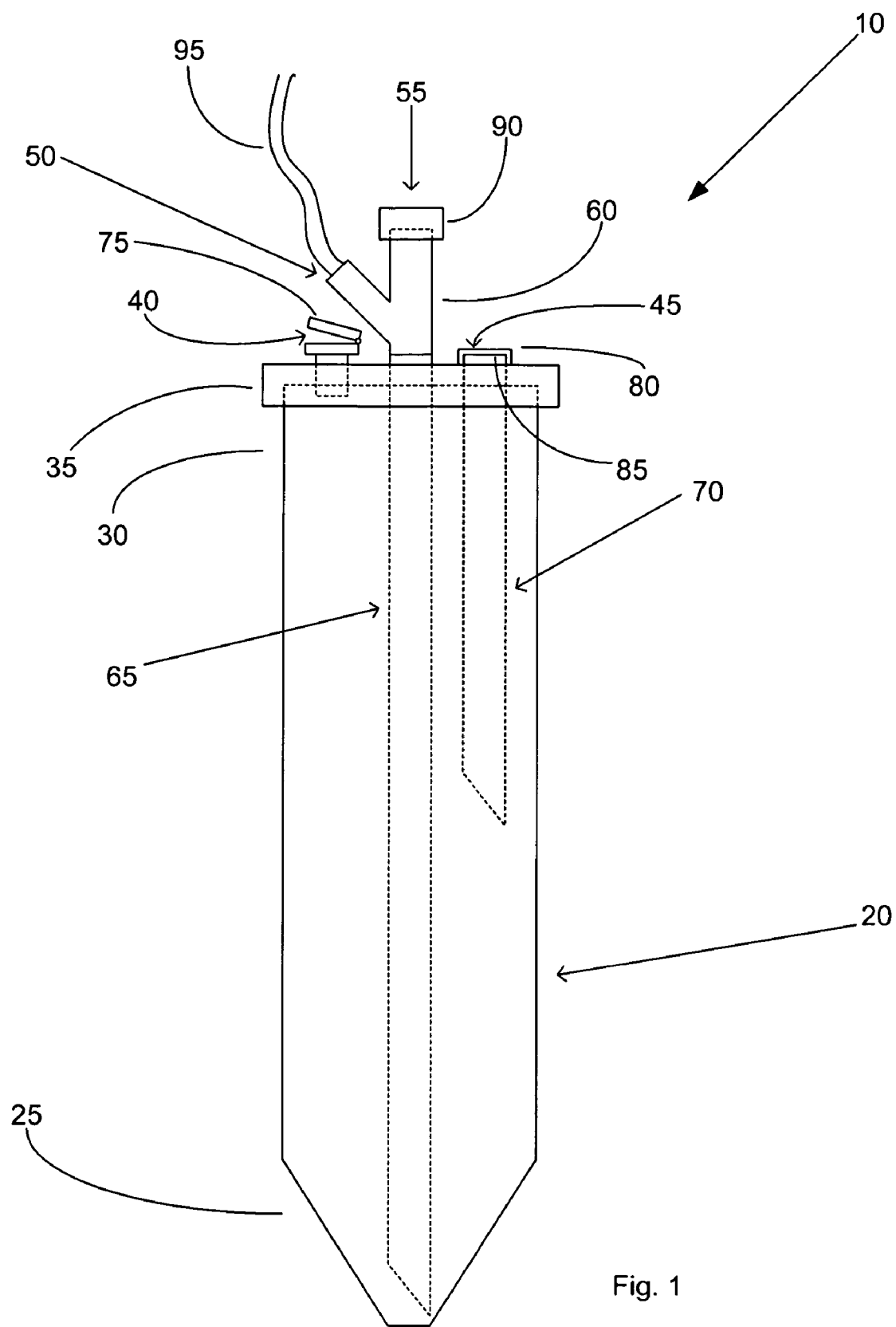
FIG. 1 is a side perspective view of one preferred embodiment of a cell washing device of the present invention.

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

As shown in FIG. 1, the cell washing device 10 comprises a relatively small volume, test-tube shaped container 20 having a closed bottom end 25 and an open top end 30. While the volume of the container 20 should equal to less than the volume of a standard unit of RBC's, 250 ml to 350 ml, the preferred volume of the container for newborn transfusions is about 50 ml. The closed bottom end 25 may be round, conical, or flat bottomed, however a conical or partially conical shape is preferred to maximize withdrawal of washed RBC's. The container 20 is preferably graduated in 5 ml increments and constructed of polypropylene, modified polystyrene, or other biocompatible material.

A cap 35 is secured upon the open end 30 of the container 20. The cap is preferably of the screw on variety, however, any airtight seal could be employed. Disposed through the cap 35 are several ports, including a vent port 40, a suction port 45, an inlet port 50, and an injection/sampling port 55. In one preferred embodiment, the inlet port 50 and the injection/sampling port 55 are combined in a y-type fitting 60.

Vent port 40 comprises a re-sealable cap 75. The re-sealable cap 75 may have a hinged top that can be manually opened and closed or may have some type of check valve arrangement. The manual hinged top design is preferred, however, to minimize the cost associated with manufacturing the device. The vent port 40 may be opened to allow injection of RBC's and saline solution and to allow the removal of the supernatant and dispensing of the washed RBC's. Vent port 40 may also be fitted with a hydrophobic polytetrafluoroethylene (PTFE) filter, a glass/monofilament polyester fiber filter, or an equivalent filter. If a filter is employed, the preferred pore size from about 0.22 µm to about 0.4 µm.

Suction port 45 comprises a cap 80 that is removable from suction port 45 and an adapter 85 traversing through cap 35. Adapter 85 is capable of being connected to tubing that is employed to remove the supernatant after centrifugation.

In the preferred embodiment illustrated in FIG. 1, inlet port 50 and injection/sampling port 55 are combined in a y-shaped fitting 60. The injection/sampling port 55 portion of the y-shaped fitting 60 is preferable fitted with a cap 90 having a membrane surface for the insertion of a plain tip syringe, or alternatively may be fitted with a locking device, such as a Luer-Lock or Luer-Slip tip, which couples to the a locking tip syringe.

A clear, rigid tube 65 projects downward from the y-type fitting, through the cap 35 and into container 20. Tube 65 extends downward into the container 20 and ends substantially near the bottom end 25. Tube 65 serves as a conduit for the injection of RBC's into container 20, for the injection of saline solution, and for the dispensing of washed RBC's. Another clear, rigid tube 70 projects downward from the suction port 45. Tube 70 serves as a conduit for removing the supernatant after centrifugation. Both tube 65 and tube 70 may be constructed of polystyrene or other suitable material.

In addition to the device described above, a centrifuge, a suction pump, and a sterile tube connector device for connecting the device to a blood unit are also required.

The preferred procedure for using the present invention is as follows: First, the container 20 should be labeled with standard required information, such as the patient name, hospital number, unit number, etc. Using a sterile technique, approximately 25 ml of RBC's should be delivered from the main blood unit via tubing 95 through inlet port 50 and into the container 20 via tube 65. After the RBC's have been transferred, approximately 25 ml of saline solution should be injected through injection/sampling port 55 and into the container 20 via tube 65. Container 25 is then placed within a centrifuge operating at about 1500 to about 1600 rpm for approximately 15 minutes. After centrifugation, the container 20 is carefully removed from the centrifuge and the caps 75, 80 are opened or removed from the vent port 40 and the suction port 45. Suction tubing from a suction pump is attached to adapter 85 in the suction port 45. The suction pump is preferably set for about 100 mm Hg and the supernatant is carefully removed from container 20 via tube 70. After suctioning off the supernatant, suction port 45 is sealed with cap 80. A syringe is then employed to remove the washed blood product through injection/sampling port 55 from container 20 via tube 65.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A device for washing blood product with a washing solution comprising: a container having a closed bottom end and an open top end; a cap secured over the top end of the container; a first tube disposed through the cap and projecting downward into the container substantially to the closed bottom end, the first tube configured to receive the blood product and the washing solution; and a second tube disposed through the cap and projecting downward into the container, the second tube having a sealable cap and configured to remove the washing solution, wherein the first tube includes a top end having a y-shaped fitting.

2. The device of claim 1, wherein the container is cylindrical.

3. The device of claim 1, wherein the container is capable of being inserted into a centrifuge.

4. The device of claim 3, wherein the container has a volume of less than 350 milliliters.

5. The device of claim 4, wherein the container has a volume of about 50 milliliters.

6. The device of claim 5, wherein the container is constructed of polypropylene.

7. The device of claim 5, wherein the container is constructed of modified polystyrene.

8. The device of claim 1, wherein the first tube and the second tube are constructed of rigid polypropylene.

9. The device of claim 1, wherein the first tube and the second tube are constructed of rigid polystyrene.

10. The device of claim 1, wherein the cap further comprises vent.

11. The device of claim 10, wherein the vent further comprises an air filter.

12. The device of claim 11, wherein the air filter is a USP Class VI, hydrophobic air filter.

13. The device of claim 1, wherein the first tube further comprises a top end having a y-shaped fitting, the y-shaped fitting having a first top end, a second top end, and a bottom end.

14. The device of claim 13, wherein the first top end of the y-shaped fitting is capable of receiving blood product from a standard blood product unit.

15. The device of claim 13, wherein the second top end of the y-shaped fitting comprises a cap having a membrane capable of receiving a plain tip syringe.

16. The device of claim 13, wherein the second top end of the y-shaped fitting comprises a cap having a locking device capable of receiving a locking tip syringe.

17. A device for washing blood product with a washing solution comprising: a container having a closed bottom end and an open top end; a cap secured over the top end of the container; a first tube disposed through the cap and projecting downward into the container substantially to the closed bottom end, the first tube configured to receive the blood product and the washing solution; and a second tube disposed through the cap and projecting downward into the container, the second tube having a sealable cap and configured to remove the washing solution, wherein the first tube includes a top end having a y-shaped fitting, the y-shaped fitting having a first top end, a second top end, and a bottom end, the first top end of the y-shaped fitting configured to receive blood product from a blood product unit, the second top end of the y-shaped fitting including a membrane configured to receive a syringe.

* * * * *